United States Patent [19]

Caldwell

[11] Patent Number: Plant 6,144

[45] Date of Patent: Apr. 5, 1988

[54] SPATHIPHYLLUM NAMED 'KELLY'

[75] Inventor: E. Bond Caldwell, Brooksville, Fla.

[73] Assignee: Hartman's Plants, Inc., Sebring, Fla.

[21] Appl. No.: 815,686

[22] Filed: Jan. 2, 1986

[51] Int. Cl.[4] ..... A01H 5/00

[52] U.S. Cl. ..... Plt./88

[58] Field of Search ..... Plt./88

*Primary Examiner*—James R. Feyrer

*Attorney, Agent, or Firm*—Irving N. Feit

[57] ABSTRACT

Disclosed is a new and distinct Spathiphyllum variety distinguished particularly by rapid growth, denser appearance and compact growth when compared to related plants. Spathe color is initially white turning a light green hue past maturity.

1 Drawing Sheet

The invention comprises a new and distinct cultivar of Spathiphyllum known as Spathiphyllum hybrida 'Kelly'.

The new cultivar is a product of a random breeding program carried out by Bond Caldwell of Babylon Nursery, Brooksville, Fla. The parents are unknown. The cultivar was discovered and selected from the progeny of the random cross by Mr. Caldwell. Asexual propagation by division (Mr. Caldwell) and by tissue culture (Hartman's Plants, Inc.), Palmdale, Fla. was used to increase the number of plants available for evaluation and to demonstrate the stability of the distinguishing combination of characteristics from generation to generation.

The following observations, measurements and values describe plants grown in Brooksville under greenhouse conditions that closely approximate those generally used in horticultural practice.

The following traits have been repeatedly observed, and are characteristics that in combination distinguish Spathiphyllum hybrida 'Kelly' from other Spathiphyllum of the same general type i.e.; 'Supreme', 'Lynise' and 'St. Mary's'. Mauna loa 'Supreme' and 'St. Mary's' are trademarks of Olgesby Lab, Inc.

DISTINCTIONS

1. Dense spreading habit that is shorter and wider than 'Supreme', 'Lynise' and 'St. Mary's'.
2. Suckers more than 'St. Mary's'.
3. Reaches mature size faster than 'Supreme', or 'Lynise' or 'St. Mary's'.
4. Leaf is broader than 'Supreme' or 'Lynise' and has prostrate tendencies that contribute to a denser appearing plant.
5. Color lighter than 'Supreme' or 'St. Mary's'.
6. Less shiny than 'Supreme' or 'St. Mary's'.
7. White flowers, the spathe being approximately 18 cm to 24 cm high and 9 cm to 12 cm wide standing above the foliage by approximately 17.5 cm to 25 cm when established in 15 gallon container.

BRIEF DESCRIPTION OF THE DRAWING

The single FIGURE of the drawing depicts a mature specimen of 'Kelly' in approximate side view, with 6 spathes in varied orientations and stages of maturity.

DESCRIPTION (All color references are measured against The Royal Horticultural Society Colour Chart.)

Origin: Seedling.

Classification: Spathiphyllum hybrida 'Kelly'.

Propagation: Asexual reproduction either through tissue culture or division.

Plant:

In a 15 gal pot, 'Kelly' is, at mature size, approximately 0.6 meters to 0.9 meters high and approximately 1.1 meters to 1.4 meters wide after approximately 45 weeks to 55 weeks under the appropriate growing conditions from tissue culture.

Leaves:

*Form and size.*—Simple elliptic with an apice having aristate tendencies and a cuneate base.

*Leaf blade size and width.*—Leaves of a mature sized plant will be approximately 30 cm to 45 cm in length and approximately 15 cm to 25 cm in width.

*Texture.*—Less glossy than 'Supreme' and 'St. Mary's'. Less stiff than 'Lynise'.

*Veins.*—Well defined widely spaced sunken veins.

*Color.*—Mature leaf. Adaxial side 137B. Abaxial side 191A, 191B. Immature leaf. Adaxial side 138A. Abaxial side 143C, 144A.

*Leaf height.*—Approximately 0.6 meters to 0.9 meters from soil surface.

Inflorescence:

*Immature.*—The spathe is tightly rolled around the spadix and extrudes from the petiole sheath. The spathe is fully open approximately when the pedicel is fully elongated-approximately 0.9 meters to 1.1 meters from the soil surface.

Spathe:

*Size.*—The spathe is approximately 18 cm to 24 cm high and approximately 9 cm to 12 cm in width.

*Color.*—the color is 155D turning to 138B as the spathe matures.

*Arrangement.*—The spathe stands up on straight wiry pedicles and opens vertically above the leaves.

*Shape.*—The spathe is oval with an aristate apice. It is slightly cupped and is approximately 18 cm to 24 cm high and approximately 9 cm to 12 cm wide.

*Flowering time.*—After approximately 8 months to 10 months for an untreated plant depending on season approximately 1 to 3 blossoms will be present. Smaller blossoms may occur on less mature growth.

Reproductive organs:

*Spadix.*—Size. Approximately 9 cm to 12 cm high and approximately 12 mm to 20 mm in diameter. Color: When the spathe unrolls, the spadix is 158C gradually changing to 147A.

*Stamens.*—Anthers and filaments are not clearly visible.

*Pollen.*—158C in color.

*Pistil.*—158C in color, protruding between the staminate flowers, firmly fixed to the main axle. The pistilate flowers extend approximately 2 mm to 4 mm beyond the staminate flowers.

Roots: White fleshy main roots with fine laterals.

GENERAL OBSERVATIONS

Spathiphyllum 'Kelly' is a faster growing cultivar than 'Supreme', 'Lynise' or 'St. Mary's'. It presents a denser appearance than 'Supreme', 'Lynise' or 'St. Mary's'. It is somewhat shorter than 'Supreme', 'Lynise' or 'St. Mary's'. 'Kelly', in combination with the characteristics described above, is a unique new cultivar.

I claim:

1. A new and distinct cultivar of Spathiphyllum as described and illustrated.

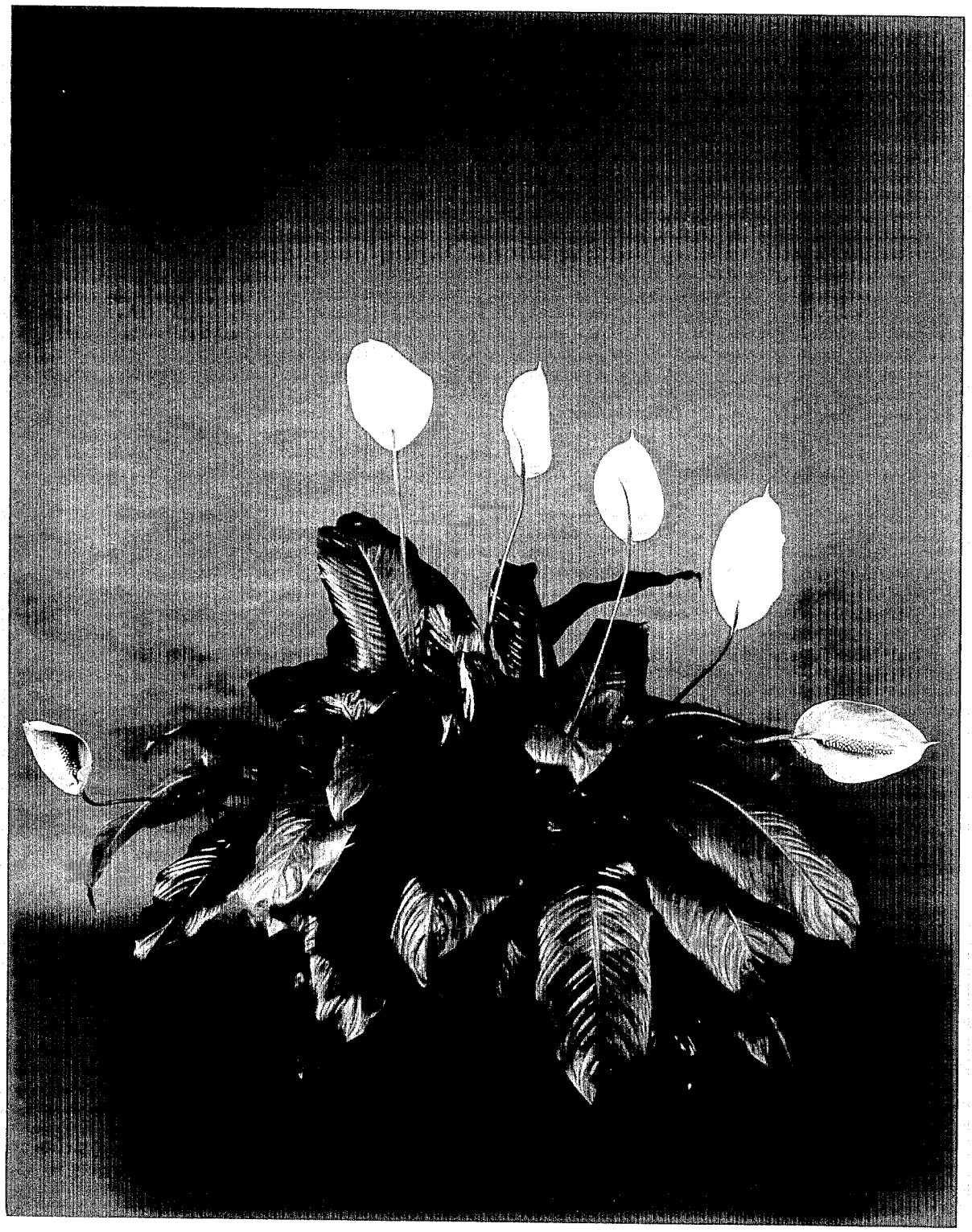

* * * * *